(12) United States Patent
Nunn et al.

(10) Patent No.: US 10,182,661 B2
(45) Date of Patent: Jan. 22, 2019

(54) INFLATABLE AIR MATTRESS ALERT AND MONITORING SYSTEM

(71) Applicants: Sleep Number Corporation, Minneapolis, MN (US); Select Comfort Retail Corporation, Minneapolis, MN (US)

(72) Inventors: Rob Nunn, Eden Prairie, MN (US); Wade Daniel Palashewski, Andover, MN (US); Matthew Wayne Tilstra, Rogers, MN (US); Stacy Stusynski, Blaine, MN (US); Steven Young, Campbell, CA (US); Carl Hewitt, Campbell, CA (US)

(73) Assignee: Sleep Number Corporation and Select Comfort Retail Corporation, Minneapolis, MN (US)

( * ) Notice: Subject to any disclaimer, the term of this patent is extended or adjusted under 35 U.S.C. 154(b) by 821 days.

(21) Appl. No.: 14/209,222

(22) Filed: Mar. 13, 2014

(65) Prior Publication Data

US 2014/0259433 A1    Sep. 18, 2014

Related U.S. Application Data

(60) Provisional application No. 61/781,266, filed on Mar. 14, 2013.

(51) Int. Cl.
*A47C 27/08* (2006.01)
*A47C 31/00* (2006.01)
(Continued)

(52) U.S. Cl.
CPC ............ *A47C 27/083* (2013.01); *A47C 31/00* (2013.01); *A47C 27/082* (2013.01); *A47C 27/10* (2013.01); *A61B 5/1115* (2013.01); *A61B 5/6892* (2013.01)

(58) Field of Classification Search
CPC ..... A47C 27/083; A47C 27/082; A47C 27/10; A47C 27/088; A47C 27/15; A47C 27/04;
(Continued)

(56) References Cited

U.S. PATENT DOCUMENTS 3,727,606 A    4/1973   Sielaff
4,146,885 A    3/1979   Lawson, Jr.
(Continued)

FOREIGN PATENT DOCUMENTS

JP    2004/049388         2/2004
JP    2004-229875 A       8/2004
(Continued)

OTHER PUBLICATIONS

U.S. Appl. No. 14/687,633, filed Apr. 15, 2015, Brosnan et al.
(Continued)

*Primary Examiner* — Nicholas F Polito
*Assistant Examiner* — Morgan J McClure
(74) *Attorney, Agent, or Firm* — Fish & Richardson P.C.

(57) ABSTRACT

This disclosure describes, among other things, techniques for waking a user by changing the user's sleep environment. In one example, a method includes receiving, at a central controller of an air mattress system, at least one user alarm setting, generating, via the central controller, at least one instruction based on the received user alarm setting, and transmitting, from the central controller, the at least one instruction to a first component of the air mattress system to adjust a feature of the first component.

26 Claims, 7 Drawing Sheets

(51) Int. Cl.
 *A61B 5/11* (2006.01)
 *A47C 27/10* (2006.01)
 *A61B 5/00* (2006.01)

(58) Field of Classification Search
 CPC ..... A47C 27/042; A47C 27/085; A47C 27/18; A47C 31/00; A47C 31/123; A47C 31/008; A61B 5/1115; A61B 5/024; A61B 5/002; A61B 5/0816; A61B 5/11; A61B 5/6892; A61B 5/6891; A61B 5/1113
 See application file for complete search history.

(56) References Cited

U.S. PATENT DOCUMENTS

| | | | |
|---|---|---|---|
| 4,299,233 A | 11/1981 | Lemelson | |
| 4,438,771 A | 3/1984 | Friesen et al. | |
| 4,657,026 A | 4/1987 | Tagg | |
| 4,662,012 A | 5/1987 | Torbet | |
| 4,766,628 A | 8/1988 | Greer et al. | |
| 4,788,729 A | 12/1988 | Greer et al. | |
| 4,829,616 A | 5/1989 | Walker | |
| 4,890,344 A | 1/1990 | Walker | |
| 4,897,890 A | 2/1990 | Walker | |
| 4,908,895 A | 3/1990 | Walker | |
| 4,982,466 A | 1/1991 | Higgins et al. | |
| 4,991,244 A | 2/1991 | Walker | |
| 5,020,176 A | 6/1991 | Dotson | |
| 5,062,169 A | 11/1991 | Kennedy et al. | |
| 5,144,706 A | 9/1992 | Walker et al. | |
| 5,170,522 A | 12/1992 | Walker | |
| 5,197,490 A | 3/1993 | Steiner et al. | |
| 5,459,452 A | 10/1995 | DePonte | |
| 5,487,196 A * | 1/1996 | Wilkinson | A61G 7/001 5/710 |
| 5,509,154 A | 4/1996 | Shafer et al. | |
| 5,515,865 A | 5/1996 | Scanlon | |
| 5,564,140 A | 10/1996 | Shoenhair et al. | |
| 5,642,546 A | 6/1997 | Shoenhair | |
| 5,652,484 A | 7/1997 | Shafer et al. | |
| 5,675,855 A | 10/1997 | Culp | |
| 5,684,460 A | 11/1997 | Scanlon | |
| 5,699,038 A | 12/1997 | Ulrich et al. | |
| 5,724,990 A | 3/1998 | Ogino | |
| 5,765,246 A | 6/1998 | Shoenhair | |
| 5,771,511 A | 6/1998 | Kummer et al. | |
| 5,796,340 A | 8/1998 | Miller | |
| 5,844,488 A | 12/1998 | Musick | |
| 5,848,450 A | 12/1998 | Oexman et al. | |
| 5,903,941 A | 5/1999 | Shafer et al. | |
| 5,904,172 A | 5/1999 | Gifft et al. | |
| 5,948,303 A * | 9/1999 | Larson | G05D 23/1905 126/205 |
| 5,964,720 A | 10/1999 | Pelz | |
| 5,989,193 A | 11/1999 | Sullivan | |
| 6,024,699 A | 2/2000 | Surwit et al. | |
| 6,037,723 A | 3/2000 | Shafer et al. | |
| 6,058,537 A | 5/2000 | Larson | |
| 6,062,216 A | 5/2000 | Corn | |
| 6,094,762 A | 8/2000 | Viard et al. | |
| 6,108,844 A | 8/2000 | Kraft et al. | |
| 6,120,441 A | 9/2000 | Griebel | |
| 6,146,332 A | 11/2000 | Pinsonneault et al. | |
| 6,147,592 A | 11/2000 | Ulrich et al. | |
| 6,161,231 A | 12/2000 | Kraft et al. | |
| 6,202,239 B1 | 3/2001 | Ward et al. | |
| 6,208,250 B1 | 3/2001 | Dixon et al. | |
| 6,234,642 B1 | 5/2001 | Bokaemper | |
| 6,272,378 B1 | 8/2001 | Baumgart-Schmitt | |
| 6,320,510 B2 * | 11/2001 | Menkedick | A61G 7/05 340/5.1 |
| 6,386,201 B1 | 5/2002 | Fard | |
| 6,396,224 B1 * | 5/2002 | Luff | A47C 20/048 318/16 |
| 6,397,419 B1 | 6/2002 | Mechache | |
| 6,438,776 B2 | 8/2002 | Ferrand et al. | |
| 6,450,957 B1 | 9/2002 | Yoshimi et al. | |
| 6,468,234 B1 | 10/2002 | Ford et al. | |
| 6,483,264 B1 | 11/2002 | Shafer et al. | |
| 6,485,441 B2 | 11/2002 | Woodward | |
| 6,546,580 B2 | 4/2003 | Shimada | |
| 6,547,743 B2 | 4/2003 | Brydon | |
| 6,561,047 B1 | 5/2003 | Gladney | |
| 6,566,833 B2 | 5/2003 | Bartlett | |
| 6,686,711 B2 | 2/2004 | Rose et al. | |
| 6,707,386 B1 * | 3/2004 | Pruisner | G08B 13/10 307/116 |
| 6,708,357 B2 | 3/2004 | Gaboury et al. | |
| 6,719,708 B1 | 4/2004 | Jansen | |
| 6,763,541 B2 | 7/2004 | Mahoney et al. | |
| 6,778,090 B2 | 8/2004 | Newham | |
| 6,804,848 B1 | 10/2004 | Rose | |
| 6,832,397 B2 | 12/2004 | Gaboury et al. | |
| 6,840,117 B2 | 1/2005 | Hubbard, Jr. | |
| 6,840,907 B1 | 1/2005 | Brydon | |
| 6,847,301 B1 | 1/2005 | Olson | |
| 6,878,121 B2 | 4/2005 | Krausman | |
| 6,883,191 B2 | 5/2005 | Gaboury et al. | |
| 6,993,380 B1 | 1/2006 | Modarres | |
| 7,041,049 B1 | 5/2006 | Raniere | |
| 7,077,810 B2 | 7/2006 | Lange et al. | |
| 7,150,718 B2 | 12/2006 | Okada | |
| 7,237,287 B2 | 7/2007 | Weismiller et al. | |
| 7,253,366 B2 | 8/2007 | Bhai | |
| 7,304,580 B2 | 12/2007 | Sullivan et al. | |
| 7,314,451 B2 | 1/2008 | Halperin et al. | |
| 7,321,811 B1 | 1/2008 | Rawls-Meehan | |
| 7,330,127 B2 | 2/2008 | Price et al. | |
| 7,389,554 B1 | 6/2008 | Rose | |
| 7,396,331 B2 | 7/2008 | Mack | |
| 7,429,247 B2 | 9/2008 | Okada et al. | |
| 7,437,787 B2 | 10/2008 | Bhai | |
| 7,465,280 B2 | 12/2008 | Rawls-Meehan | |
| 7,480,951 B2 | 1/2009 | Weismiller | |
| 7,506,390 B2 | 3/2009 | Dixon et al. | |
| 7,520,006 B2 | 4/2009 | Menkedick et al. | |
| 7,524,279 B2 | 4/2009 | Auphan | |
| 7,532,934 B2 | 5/2009 | Lee et al. | |
| 7,538,659 B2 | 5/2009 | Ulrich | |
| 7,568,246 B2 | 8/2009 | Weismiller et al. | |
| 7,637,859 B2 | 12/2009 | Lindback et al. | |
| 7,652,581 B2 | 1/2010 | Gentry et al. | |
| 7,666,151 B2 * | 2/2010 | Sullivan | A61B 5/11 340/573.1 |
| 7,669,263 B2 | 3/2010 | Menkedick et al. | |
| 7,676,872 B2 | 3/2010 | Block et al. | |
| 7,685,663 B2 | 3/2010 | Rawls-Meehan | |
| 7,699,784 B2 | 4/2010 | Wan et al. | |
| 7,717,848 B2 | 5/2010 | Heruth et al. | |
| 7,746,218 B2 * | 6/2010 | Collins, Jr. | A61L 35/1115 340/286.07 |
| 7,749,154 B2 | 7/2010 | Cornel | |
| 7,784,128 B2 | 8/2010 | Kramer | |
| 7,785,257 B2 | 8/2010 | Mack et al. | |
| 7,805,785 B2 | 10/2010 | Rawls-Meehan | |
| 7,841,031 B2 | 11/2010 | Rawls-Meehan | |
| 7,849,545 B2 | 12/2010 | Flocard et al. | |
| 7,854,031 B2 | 12/2010 | Rawls-Meehan | |
| 7,860,723 B2 | 12/2010 | Rawls-Meehan | |
| 7,862,523 B2 | 1/2011 | Ruotoistenmaki | |
| 7,865,988 B2 | 1/2011 | Koughan et al. | |
| 7,868,757 B2 | 1/2011 | Radivojevic et al. | |
| 7,869,903 B2 | 1/2011 | Turner et al. | |
| 7,930,783 B2 | 4/2011 | Rawls-Meehan | |
| 7,933,669 B2 | 4/2011 | Rawls-Meehan | |
| 7,953,613 B2 | 5/2011 | Gizewski | |
| 7,954,189 B2 | 6/2011 | Rawls-Meehan | |
| 7,956,755 B2 | 6/2011 | Lee et al. | |
| 7,967,739 B2 | 6/2011 | Auphan | |
| 7,979,169 B2 | 7/2011 | Rawls-Meehan | |
| 8,019,486 B2 | 9/2011 | Rawls-Meehan | |
| 8,020,230 B2 | 9/2011 | Rawls-Meehan | |
| 8,028,363 B2 | 10/2011 | Rawls-Meehan | |
| 8,032,263 B2 | 10/2011 | Rawls-Meehan | |

(56) References Cited

U.S. PATENT DOCUMENTS

| | | |
|---|---|---|
| 8,032,960 B2 | 10/2011 | Rawls-Meehan |
| 8,046,114 B2 | 10/2011 | Rawls-Meehan |
| 8,046,115 B2 | 10/2011 | Rawls-Meehan |
| 8,046,116 B2 | 10/2011 | Rawls-Meehan |
| 8,046,117 B2 | 10/2011 | Rawls-Meehan |
| 8,050,805 B2 | 11/2011 | Rawls-Meehan |
| 8,052,612 B2 | 11/2011 | Tang |
| 8,065,764 B2 | 11/2011 | Kramer |
| 8,069,852 B2 | 12/2011 | Burton |
| 8,073,535 B2 | 12/2011 | Jung et al. |
| 8,078,269 B2 | 12/2011 | Suzuki et al. |
| 8,078,336 B2 | 12/2011 | Rawls-Meehan |
| 8,078,337 B2 | 12/2011 | Rawls-Meehan |
| 8,083,682 B2 | 12/2011 | Dalal et al. |
| 8,090,478 B2 | 1/2012 | Skinner et al. |
| 8,092,399 B2 | 1/2012 | Sasaki |
| 8,094,013 B1 | 1/2012 | Lee et al. |
| 8,096,960 B2 | 1/2012 | Loree, IV et al. |
| 8,144,001 B1 | 3/2012 | D'Souza |
| 8,146,191 B2 | 4/2012 | Bobey et al. |
| 8,150,562 B2 | 4/2012 | Rawls-Meehan |
| 8,166,589 B2 | 5/2012 | Hijlkema |
| 8,181,290 B2 | 5/2012 | Brykalski et al. |
| 8,181,296 B2 | 5/2012 | Rawls-Meehan |
| 8,266,742 B2 | 9/2012 | Andrienko |
| 8,272,892 B2 | 9/2012 | McNeely et al. |
| 8,276,585 B2 | 10/2012 | Buckley |
| 8,279,057 B2 | 10/2012 | Hirose |
| 8,280,748 B2 | 10/2012 | Allen |
| 8,281,433 B2 | 10/2012 | Riley et al. |
| 8,282,452 B2 | 10/2012 | Grigsby et al. |
| 8,284,047 B2 | 10/2012 | Collins, Jr. |
| 8,287,452 B2 | 10/2012 | Young et al. |
| 8,336,369 B2 | 12/2012 | Mahoney |
| 8,341,784 B2 | 1/2013 | Scott |
| 8,341,786 B2 | 1/2013 | Oexman et al. |
| 8,348,840 B2 | 1/2013 | Heit et al. |
| 8,350,709 B2 | 1/2013 | Receveur |
| 8,375,488 B2 | 2/2013 | Rawls-Meehan |
| 8,376,954 B2 | 2/2013 | Lange et al. |
| 8,382,484 B2 | 2/2013 | Wetmore et al. |
| 8,386,008 B2 | 2/2013 | Yuen et al. |
| 8,398,538 B2 | 3/2013 | Dothie |
| 8,403,865 B2 | 3/2013 | Halperin et al. |
| 8,413,274 B2 | 4/2013 | Weismiller et al. |
| 8,421,606 B2 | 4/2013 | Collins, Jr. et al. |
| 8,428,696 B2 | 4/2013 | Foo |
| 8,517,953 B2 | 4/2013 | Lange et al. |
| 8,444,558 B2 | 5/2013 | Young et al. |
| 8,620,615 B2 | 12/2013 | Oexman |
| 8,672,853 B2 | 3/2014 | Young |
| 8,679,034 B2 | 3/2014 | Halperin et al. |
| 8,769,747 B2 | 7/2014 | Mahoney et al. |
| 8,840,564 B2 | 9/2014 | Pinhas et al. |
| 8,931,329 B2 | 1/2015 | Mahoney et al. |
| 8,966,689 B2 | 3/2015 | McGuire et al. |
| 8,973,183 B1 | 3/2015 | Palashewski et al. |
| 8,984,687 B2 | 3/2015 | Stusynski et al. |
| 2002/0124311 A1 | 9/2002 | Peftoulidis |
| 2003/0045806 A1 | 3/2003 | Brydon |
| 2003/0128125 A1 | 6/2003 | Burbank et al. |
| 2003/0166995 A1 | 9/2003 | Jansen |
| 2003/0182728 A1 | 10/2003 | Chapman et al. |
| 2003/0221261 A1 | 12/2003 | Torbet et al. |
| 2004/0049132 A1 | 3/2004 | Barron et al. |
| 2005/0022606 A1 | 2/2005 | Partin et al. |
| 2005/0038326 A1 | 2/2005 | Mathur |
| 2005/0115561 A1 | 6/2005 | Stahmann et al. |
| 2005/0190068 A1 | 9/2005 | Gentry et al. |
| 2005/0283039 A1 | 12/2005 | Cornel |
| 2006/0020178 A1 | 1/2006 | Sotos et al. |
| 2006/0031996 A1 | 2/2006 | Rawls-Meehan |
| 2006/0047217 A1 | 3/2006 | Mirtalebi |
| 2006/0152378 A1 | 7/2006 | Lokhorst |
| 2006/0162074 A1 | 7/2006 | Bader |
| 2007/0118054 A1 | 5/2007 | Pinhas et al. |
| 2007/0149883 A1 | 6/2007 | Yesha |
| 2007/0179334 A1 | 8/2007 | Groves et al. |
| 2007/0180047 A1 | 8/2007 | Dong et al. |
| 2007/0180618 A1 | 8/2007 | Weismiller et al. |
| 2007/0276202 A1 | 11/2007 | Raisanen et al. |
| 2008/0052837 A1* | 3/2008 | Blumberg ............ A47C 23/002 5/727 |
| 2008/0071200 A1 | 3/2008 | Rawls-Meehan |
| 2008/0077020 A1 | 3/2008 | Young et al. |
| 2008/0092291 A1 | 4/2008 | Rawls-Meehan |
| 2008/0092292 A1 | 4/2008 | Rawls-Meehan |
| 2008/0092293 A1 | 4/2008 | Rawls-Meehan |
| 2008/0092294 A1 | 4/2008 | Rawls-Meehan |
| 2008/0093784 A1 | 4/2008 | Rawls-Meehan |
| 2008/0097774 A1 | 4/2008 | Rawls-Meehan |
| 2008/0097778 A1 | 4/2008 | Rawls-Meehan |
| 2008/0097779 A1 | 4/2008 | Rawls-Meehan |
| 2008/0104750 A1 | 5/2008 | Rawls-Meehan |
| 2008/0104754 A1 | 5/2008 | Rawls-Meehan |
| 2008/0104755 A1 | 5/2008 | Rawls-Meehan |
| 2008/0104756 A1 | 5/2008 | Rawls-Meehan |
| 2008/0104757 A1 | 5/2008 | Rawls-Meehan |
| 2008/0104758 A1 | 5/2008 | Rawls-Meehan |
| 2008/0104759 A1 | 5/2008 | Rawls-Meehan |
| 2008/0104760 A1 | 5/2008 | Rawls-Meehan |
| 2008/0104761 A1 | 5/2008 | Rawls-Meehan |
| 2008/0109959 A1 | 5/2008 | Rawls-Meehan |
| 2008/0109964 A1 | 5/2008 | Flocard et al. |
| 2008/0109965 A1 | 5/2008 | Mossbeck |
| 2008/0115272 A1 | 5/2008 | Rawls-Meehan |
| 2008/0115273 A1 | 5/2008 | Rawls-Meehan |
| 2008/0115274 A1 | 5/2008 | Rawls-Meehan |
| 2008/0115275 A1 | 5/2008 | Rawls-Meehan |
| 2008/0115276 A1 | 5/2008 | Rawls-Meehan |
| 2008/0115277 A1 | 5/2008 | Rawls-Meehan |
| 2008/0115278 A1 | 5/2008 | Rawls-Meehan |
| 2008/0115279 A1 | 5/2008 | Rawls-Meehan |
| 2008/0115280 A1 | 5/2008 | Rawls-Meehan |
| 2008/0115281 A1 | 5/2008 | Rawls-Meehan |
| 2008/0115282 A1 | 5/2008 | Rawls-Meehan |
| 2008/0120775 A1 | 5/2008 | Rawls-Meehan |
| 2008/0120776 A1 | 5/2008 | Rawls-Meehan |
| 2008/0120777 A1 | 5/2008 | Rawls-Meehan |
| 2008/0120778 A1 | 5/2008 | Rawls-Meehan |
| 2008/0120779 A1 | 5/2008 | Rawls-Meehan |
| 2008/0120784 A1 | 5/2008 | Warner et al. |
| 2008/0122616 A1 | 5/2008 | Warner |
| 2008/0126122 A1 | 5/2008 | Warner et al. |
| 2008/0126132 A1 | 5/2008 | Warner |
| 2008/0127418 A1 | 6/2008 | Rawls-Meehan |
| 2008/0127424 A1 | 6/2008 | Rawls-Meehan |
| 2008/0147442 A1 | 6/2008 | Warner |
| 2008/0162171 A1 | 7/2008 | Rawls-Meehan |
| 2008/0189865 A1 | 8/2008 | Bhai |
| 2008/0275314 A1 | 11/2008 | Mack et al. |
| 2008/0281611 A1 | 11/2008 | Rawls-Meehan |
| 2008/0281612 A1 | 11/2008 | Rawls-Meehan |
| 2008/0281613 A1 | 11/2008 | Rawls-Meehan |
| 2008/0288272 A1 | 11/2008 | Rawls-Meehan |
| 2008/0288273 A1 | 11/2008 | Rawls-Meehan |
| 2008/0306351 A1 | 12/2008 | Izumi |
| 2008/0307582 A1 | 12/2008 | Flocard et al. |
| 2009/0018853 A1 | 1/2009 | Rawls-Meehan |
| 2009/0018854 A1 | 1/2009 | Rawls-Meehan |
| 2009/0018855 A1 | 1/2009 | Rawls-Meehan |
| 2009/0018856 A1 | 1/2009 | Rawls-Meehan |
| 2009/0018857 A1 | 1/2009 | Rawls-Meehan |
| 2009/0018858 A1 | 1/2009 | Rawls-Meehan |
| 2009/0024406 A1 | 1/2009 | Rawls-Meehan |
| 2009/0037205 A1 | 2/2009 | Rawls-Meehan |
| 2009/0043595 A1 | 2/2009 | Rawls-Meehan |
| 2009/0064420 A1 | 3/2009 | Rawls-Meehan |
| 2009/0100599 A1 | 4/2009 | Rawls-Meehan |
| 2009/0121660 A1 | 5/2009 | Rawls-Meehan |
| 2009/0139029 A1 | 6/2009 | Rawls-Meehan |
| 2009/0203972 A1 | 8/2009 | Heneghan et al. |
| 2009/0275808 A1 | 11/2009 | DiMaio et al. |
| 2009/0314354 A1 | 12/2009 | Chaffee |

(56) References Cited

U.S. PATENT DOCUMENTS

| | | |
|---|---|---|
| 2010/0025900 A1 | 2/2010 | Rawls-Meehan |
| 2010/0090383 A1 | 4/2010 | Rawls-Meehan |
| 2010/0094139 A1 | 4/2010 | Brauers et al. |
| 2010/0099954 A1 | 4/2010 | Dickinson et al. |
| 2010/0152546 A1 | 6/2010 | Behan et al. |
| 2010/0170043 A1 | 7/2010 | Young et al. |
| 2010/0174198 A1 | 7/2010 | Young |
| 2010/0174199 A1 | 7/2010 | Young et al. |
| 2010/0191136 A1 | 7/2010 | Wolford |
| 2010/0199432 A1 | 8/2010 | Rawls-Meehan |
| 2010/0231421 A1 | 9/2010 | Rawls-Meehan |
| 2010/0302044 A1 | 12/2010 | Chacon et al. |
| 2010/0317930 A1 | 12/2010 | Oexman et al. |
| 2011/0001622 A1 | 1/2011 | Gentry |
| 2011/0010014 A1 | 1/2011 | Oexman et al. |
| 2011/0015495 A1 | 1/2011 | Dothie et al. |
| 2011/0041592 A1 | 2/2011 | Schmoeller et al. |
| 2011/0043359 A1* | 2/2011 | Toler ............ A61B 5/1115 340/539.15 |
| 2011/0068935 A1 | 3/2011 | Riley et al. |
| 2011/0087113 A1 | 4/2011 | Mack et al. |
| 2011/0094041 A1 | 4/2011 | Rawls-Meehan |
| 2011/0115635 A1 | 5/2011 | Petrovski et al. |
| 2011/0144455 A1 | 6/2011 | Young et al. |
| 2011/0156915 A1 | 6/2011 | Brauers et al. |
| 2011/0163885 A1 | 7/2011 | Poulos et al. |
| 2011/0224510 A1 | 9/2011 | Oakhill |
| 2011/0239374 A1 | 10/2011 | Rawls-Meehan |
| 2011/0252569 A1 | 10/2011 | Rawls-Meehan |
| 2011/0258784 A1 | 10/2011 | Rawls-Meehan |
| 2011/0282216 A1 | 11/2011 | Shinar et al. |
| 2011/0283462 A1 | 11/2011 | Rawls-Meehan |
| 2011/0291795 A1 | 12/2011 | Rawls-Meehan |
| 2011/0291842 A1 | 12/2011 | Oexman |
| 2011/0295083 A1 | 12/2011 | Doelling et al. |
| 2011/0302720 A1 | 12/2011 | Yakam et al. |
| 2011/0306844 A1 | 12/2011 | Young |
| 2012/0025992 A1 | 2/2012 | Tallent et al. |
| 2012/0053423 A1 | 3/2012 | Kenalty et al. |
| 2012/0053424 A1 | 3/2012 | Kenalty et al. |
| 2012/0056729 A1 | 3/2012 | Rawls-Meehan |
| 2012/0057685 A1 | 3/2012 | Rawls-Meehan |
| 2012/0090698 A1 | 4/2012 | Giori et al. |
| 2012/0110738 A1 | 5/2012 | Rawls-Meehan |
| 2012/0110739 A1 | 5/2012 | Rawls-Meehan |
| 2012/0110740 A1 | 5/2012 | Rawls-Meehan |
| 2012/0112890 A1 | 5/2012 | Rawls-Meehan |
| 2012/0112891 A1 | 5/2012 | Rawls-Meehan |
| 2012/0112892 A1 | 5/2012 | Rawls-Meehan |
| 2012/0116591 A1 | 5/2012 | Rawls-Meehan |
| 2012/0119886 A1 | 5/2012 | Rawls-Meehan |
| 2012/0119887 A1 | 5/2012 | Rawls-Meehan |
| 2012/0138067 A1 | 6/2012 | Rawls-Meehan |
| 2012/0154155 A1 | 6/2012 | Brasch |
| 2012/0186019 A1 | 7/2012 | Rawls-Meehan |
| 2012/0198632 A1 | 8/2012 | Rawls-Meehan |
| 2012/0311790 A1 | 12/2012 | Nomura et al. |
| 2013/0160212 A1 | 6/2013 | Oexman et al. |
| 2013/0174347 A1 | 7/2013 | Oexman et al. |
| 2013/0227787 A1 | 9/2013 | Herbst et al. |
| 2014/0007656 A1 | 1/2014 | Mahoney |
| 2014/0137332 A1 | 5/2014 | McGuire et al. |
| 2014/0182061 A1 | 7/2014 | Zaiss |
| 2014/0250597 A1 | 9/2014 | Chen et al. |
| 2014/0257571 A1 | 9/2014 | Chen et al. |
| 2014/0259417 A1 | 9/2014 | Nunn et al. |
| 2014/0259418 A1 | 9/2014 | Nunn et al. |
| 2014/0259419 A1 | 9/2014 | Stusynski |
| 2014/0259431 A1 | 9/2014 | Fleury |
| 2014/0259434 A1 | 9/2014 | Nunn et al. |
| 2014/0277611 A1 | 9/2014 | Nunn et al. |
| 2014/0277778 A1 | 9/2014 | Nunn et al. |
| 2014/0277822 A1 | 9/2014 | Nunn et al. |
| 2014/0313700 A1 | 10/2014 | Connell et al. |
| 2015/0008710 A1 | 1/2015 | Young et al. |
| 2015/0025327 A1 | 1/2015 | Young et al. |
| 2015/0026896 A1 | 1/2015 | Fleury et al. |
| 2015/0136146 A1 | 5/2015 | Hood et al. |
| 2015/0157137 A1 | 6/2015 | Nunn et al. |
| 2015/0157519 A1 | 6/2015 | Stusynski et al. |
| 2015/0182033 A1 | 7/2015 | Brosnan et al. |
| 2015/0182397 A1 | 7/2015 | Palashewski et al. |
| 2015/0182399 A1 | 7/2015 | Palashewski et al. |
| 2015/0182418 A1 | 7/2015 | Zaiss |

FOREIGN PATENT DOCUMENTS

| | | |
|---|---|---|
| WO | WO-2004/082549 A1 | 9/2004 |
| WO | WO 2008/128250 | 10/2008 |
| WO | WO-2009/108228 A1 | 9/2009 |
| WO | WO 2009/123641 | 10/2009 |

OTHER PUBLICATIONS

U.S. Appl. No. 14/675,355, filed Mar. 31, 2015, Palashewski et al.
U.S. Appl. No. 14/283,675, filed May 21, 2014, Mahoney et al.
U.S. Appl. No. 13/933,285, filed Jul. 2, 2013, Palashewski.
U.S. Appl. No. 14/146,281, filed Jan. 2, 2014, Palashewski et al.
U.S. Appl. No. 14/146,327, filed Jan. 2, 2014, Palashewski et al.
International Application Serial No. PCT/US2014/027752, International Search Report dated Jul. 15, 2014, 5 pages.
International Application Serial No. PCT/US2014/026568, International Search Report dated May 26, 2014, 3 pages.
International Application Serial No. PCT/US2014/026390, International Search Report dated May 26, 2014, 4 pages.
International Application Serial No. PCT/US2014/026347, International Search Report dated Jun. 27, 2014, 6 pages.
"International Application Serial No. PCT/US2014/024891, International Search Report dated May 15, 2014", 4 pgs.
"International Application Serial No. PCT/US2014/024891, Written Opinion dated May 15, 2014", 4 pgs.
"International Application Serial No. PCT/US2014/026288, International Search Report dated May 15, 2014", 4 pgs.
"International Application Serial No. PCT/US2014/026288, Written Opinion dated May 15, 2014", 4 pgs.
"International Application Serial No. PCT/US2014/026526, International Search Report dated May 15, 2014", 3 pgs.
"International Application Serial No. PCT/US2014/026526, Written Opinion dated May 15, 2014", 4 pgs.

* cited by examiner

INFLATABLE AIR MATTRESS ALERT AND MONITORING SYSTEM

This application claims the benefit of priority of U.S. Provisional Application No. 61/781,266 titled, "INFLATABLE AIR MATTRESS ALARM AND MONITORING SYSTEM" to Rob Nunn and filed on Mar. 14, 2013, the entire content being incorporated herein by reference in its entirety.

CROSS-REFERENCES

The subject matter described in this application is related to subject matter disclosed in the following applications: U.S. application Ser. No. 61/781,503, filed on Mar. 14, 2013, titled "INFLATABLE AIR MATTRESS SYSTEM ARCHITECTURE"; U.S. application Ser. No. 61/781,541, filed on Mar. 14, 2013, titled "INFLATABLE AIR MATTRESS AUTOFILL AND OFF BED PRESSURE ADJUSTMENT"; U.S. application Ser. No. 61/781,571, filed on Mar. 14, 2013, titled "INFLATABLE AIR MATTRESS SLEEP ENVIRONMENT ADJUSTMENT AND SUGGESTIONS"; U.S. application Ser. No. 61/782,394, filed on Mar. 14, 2013, titled "INFLATABLE AIR MATTRESS SNORING DETECTION AND RESPONSE"; U.S. application Ser. No. 61/781,296, filed on Mar. 14, 2013, titled "INFLATABLE AIR MATTRESS WITH LIGHT AND VOICE CONTROLS"; U.S. application Ser. No. 61/781,311, filed on Mar. 14, 2013, titled "INFLATABLE AIR MATTRESS SYSTEM WITH DETECTION TECHNIQUES." The contents of each of the above-references U.S. patent applications are herein incorporated by reference in their entirety.

TECHNICAL FIELD

This patent document pertains generally to mattresses and more particularly, but not by way of limitation, to an inflatable air mattress system.

BACKGROUND

Air bed systems, such as the one described in U.S. Pat. No. 5,904,172 which is incorporated herein by reference in its entirety, generally allow a user to select a desired pressure for each air chamber within the mattress. Upon selecting the desired pressure, a signal is sent to a pump and valve assembly in order to inflate or deflate the air bladders as necessary in order to achieve approximately the desired pressure within the air bladders.

In various examples, an air mattress control system allows a user to adjust the firmness or position of an air mattress bed. The mattress may have more than one zone thereby allowing a left and right side of the mattress to be adjusted to different firmness levels. Additionally, the bed may be adjustable to different positions. For example, the head section of the bed may be raised up while the foot section of the bed stays in place. In various examples, two separate remote controls are used to adjust the position and firmness, respectively.

BRIEF DESCRIPTION OF DRAWINGS

Some embodiments are illustrated by way of example and not limitation in the figures of the accompanying drawings in which.

DETAILED DESCRIPTION

Figure 1:
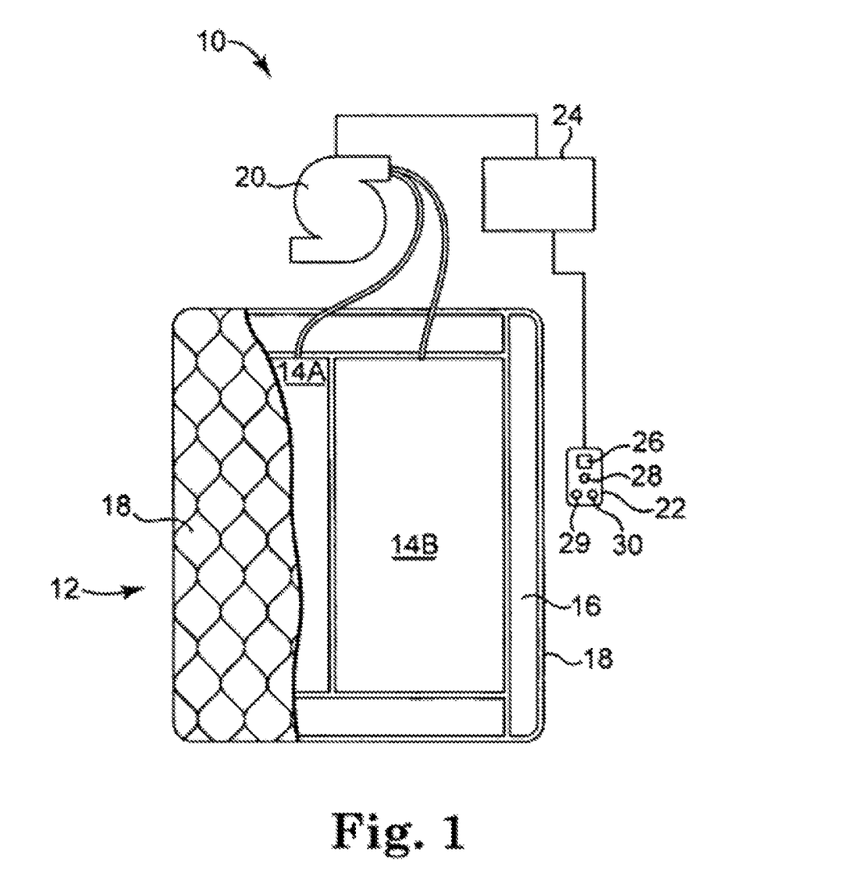
FIG. 1 is a diagrammatic representation of an air bed system, according to an example.

FIG. 1 is a diagrammatic representation of air bed system 10 in an example embodiment. System 10 can include bed 12, which can comprise at least one air chamber 14 surrounded by a resilient border 16 and encapsulated by bed ticking 18. The resilient border 16 can comprise any suitable material, such as foam.

As illustrated in FIG. 1, bed 12 can be a two chamber design having a first air chamber 14A and a second air chamber 14B. First and second air chambers 14A and 14B can be in fluid communication with pump 20. Pump 20 can be in electrical communication with a remote control 22 via control box 24. Remote control 22 can communicate via wired or wireless means with control box 24. Control box 24 can be configured to operate pump 20 to cause increases and decreases in the fluid pressure of first and second air chambers 14A and 14B based upon commands input by a user through remote control 22. Remote control 22 can include display 26, output selecting means 28, pressure increase button 29, and pressure decrease button 30. Output selecting means 28 can allow the user to switch the pump output between the first and second air chambers 14A and 14B, thus enabling control of multiple air chambers with a single remote control 22. For example, output selecting means may by a physical control (e.g., switch or button) or an input control displayed on display 26. Alternatively, separate remote control units can be provided for each air chamber and may each include the ability to control multiple air chambers. Pressure increase and decrease buttons 29 and 30 can allow a user to increase or decrease the pressure, respectively, in the air chamber selected with the output selecting means 28. Adjusting the pressure within the selected air chamber can cause a corresponding adjustment to the firmness of the air chamber.

Figure 2:
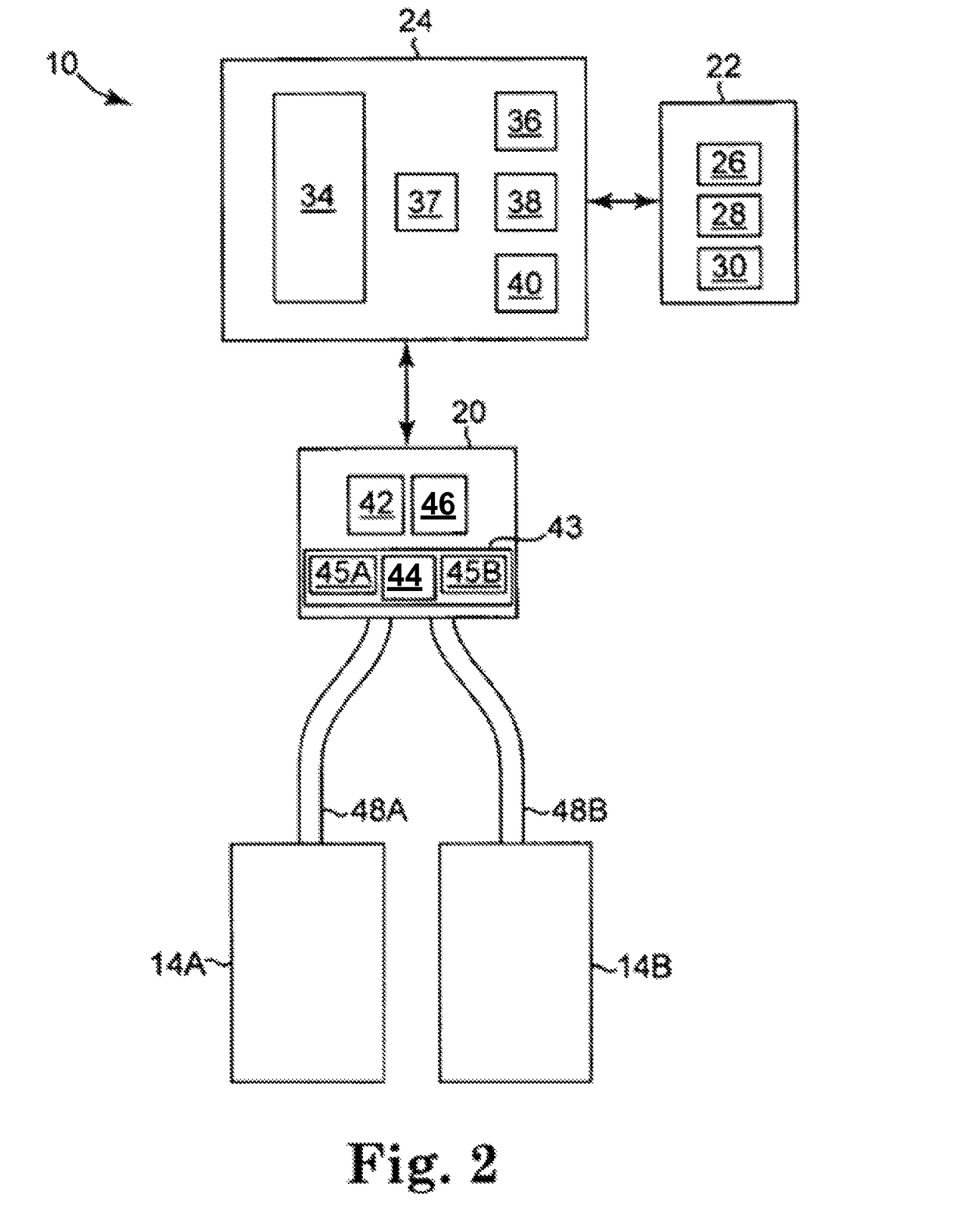
FIG. 2 is a block diagram of various components of the air bed system of FIG. 1, according to an example.

FIG. 2 is a block diagram detailing data communication between certain components of air bed system 10 according to various examples. As shown in FIG. 2, control box 24 can include power supply 34, processor 36, memory 37, switching means 38, analog to digital (A/D) converter 40, and radios for communication with remotes and smartphones. Switching means 38 can be, for example, a relay or a solid state switch. Switching means 38 can be located in the pump 20 rather than the control box 24.

Pump 20 and remote control 22 can be in two-way communication with the control box 24. Pump 20 can include a motor 42, a pump manifold 43, a relief valve 44, a first control valve 45A, a second control valve 45B, and a pressure transducer 46, and can be fluidly connected with the first air chamber 14A and the second air chamber 14B via a first tube 48A and a second tube 48B, respectively. First and second control valves 45A and 45B can be controlled by switching means 38, and can be operable to regulate the flow of fluid between pump 20 and first and second air chambers 14A and 14B, respectively.

In an example, pump 20 and control box 24 can be provided and packaged as a single unit. Alternatively, pump 20 and control box 24 can be provided as physically separate units.

In operation, power supply 34 can receive power, such as 110 VAC power, from an external source and can convert the power to various forms required by certain components of the air bed system 10. Processor 36 can be used to control various logic sequences associated with operation of the air bed system 10, as will be discussed in further detail below.

The example of the air bed system 10 shown in FIG. 2 contemplates two air chambers 14A and 14B and a single pump 20. However, other examples may include an air bed system having two or more air chambers and one or more pumps incorporated into the air bed system to control the air chambers. In an example, a separate pump can be associated with each air chamber of the air bed system or a pump may be associated with multiple chambers of the air bed system. Separate pumps can allow each air chamber to be inflated or deflated independently and simultaneously. Furthermore, additional pressure transducers can also be incorporated into the air bed system such that, for example, a separate pressure transducer can be associated with each air chamber.

In the event that the processor 36 sends a decrease pressure command to one of air chambers 14A or 14B, switching means 38 can be used to convert the low voltage command signals sent by processor 36 to higher operating voltages sufficient to operate relief valve 44 of pump 20 and open control valves 45A or 45B. Opening relief valve 44 can allow air to escape from air chamber 14A or 14B through the respective air tube 48A or 48B. During deflation, pressure transducer 46 can send pressure readings to processor 36 via the A/D converter 40. The A/D converter 40 can receive analog information from pressure transducer 46 and can convert the analog information to digital information useable by processor 36. Processor 36 may send the digital signal to remote control 22 to update display 26 on the remote control in order to convey the pressure information to the user.

In the event that processor 36 sends an increase pressure command, pump motor 42 can be energized, sending air to the designated air chamber through air tube 48A or 48B via electronically operating corresponding valve 45A or 45B. While air is being delivered to the designated air chamber in order to increase the firmness of the chamber, pressure transducer 46 can sense pressure within pump manifold 43. Again, pressure transducer 46 can send pressure readings to processor 36 via A/D converter 40. Processor 36 can use the information received from A/D converter 40 to determine the difference between the actual pressure in air chamber 14A or 14B and the desired pressure. Processor 36 can send the digital signal to remote control 22 to update display 26 on the remote control in order to convey the pressure information to the user.

Generally speaking, during an inflation or deflation process, the pressure sensed within pump manifold 43 provides an approximation of the pressure within the air chamber. An example method of obtaining a pump manifold pressure reading that is substantially equivalent to the actual pressure within an air chamber is to turn off pump 20, allow the pressure within the air chamber 14A or 14B and pump manifold 43 to equalize, and then sense the pressure within pump manifold 43 with pressure transducer 46. Thus, providing a sufficient amount of time to allow the pressures within pump manifold 43 and chamber 14A or 14B to equalize may result in pressure readings that are accurate approximations of the actual pressure within air chamber 14A or 14B. In various examples, the pressure of 48 A/B is continuously monitored using multiple pressure sensors.

In an example, another method of obtaining a pump manifold pressure reading that is substantially equivalent to the actual pressure within an air chamber is through the use of a pressure adjustment algorithm. In general, the method can function by approximating the air chamber pressure based upon a mathematical relationship between the air chamber pressure and the pressure measured within pump manifold 43 (during both an inflation cycle and a deflation cycle), thereby eliminating the need to turn off pump 20 in order to obtain a substantially accurate approximation of the air chamber pressure. As a result, a desired pressure setpoint within air chamber 14A or 14B can be achieved without the need for turning pump 20 off to allow the pressures to equalize. The latter method of approximating an air chamber pressure using mathematical relationships between the air chamber pressure and the pump manifold pressure is described in detail in U.S. application Ser. No. 12/936,084, the entirety of which is incorporated herein by reference.

Figure 3:
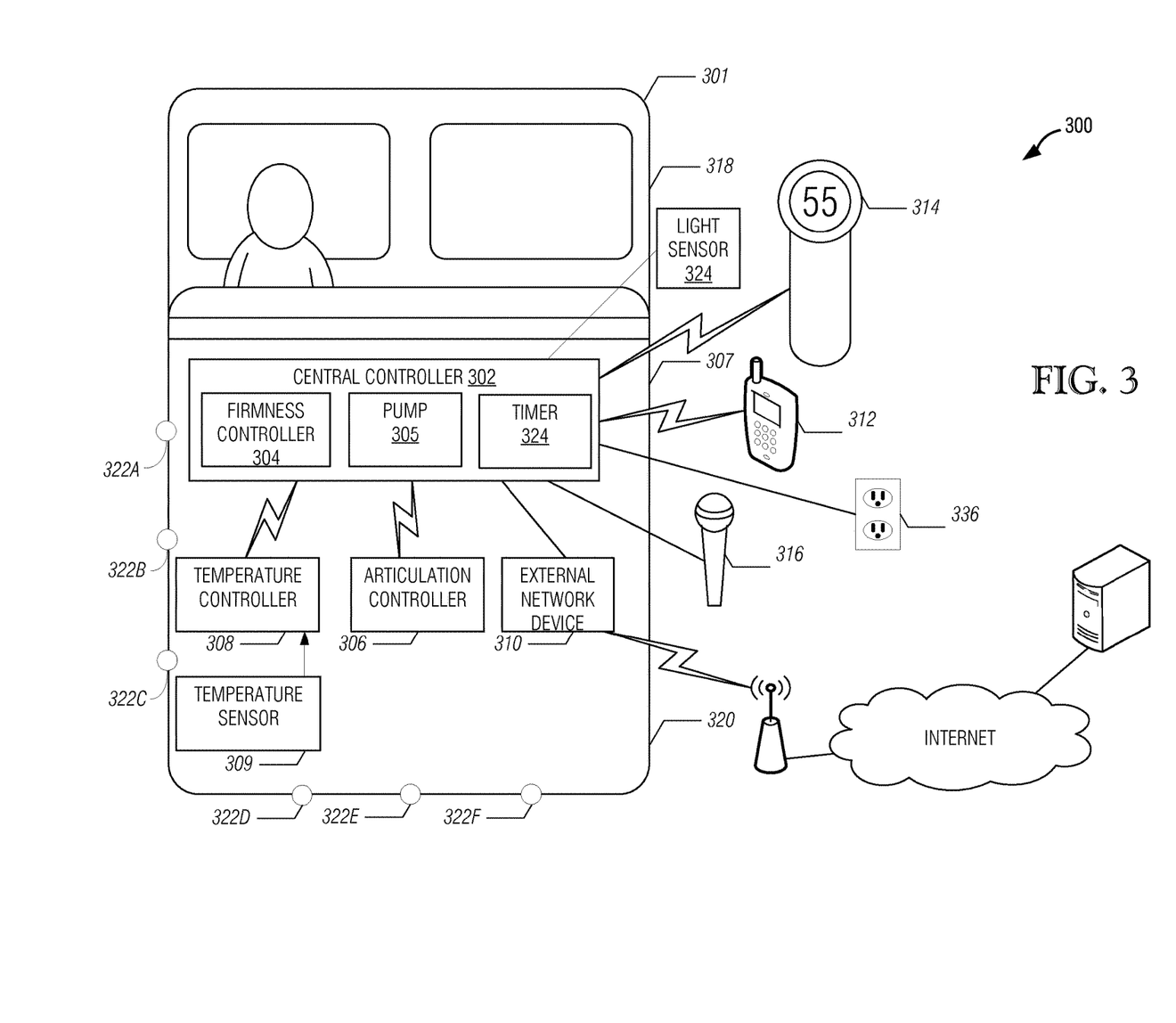
FIG. 3 is a block diagram of an air bed system architecture, according to an example.

FIG. 3 is illustrates an example air bed system architecture 300. Architecture 300 includes bed 301, central controller 302, firmness controller 304, articulation controller 306, temperature controller 308 in communication with one or more temperature sensors 309, external network device 310, remote controllers 312, 314, and voice controller 316. While described as using an air bed, the system architecture may also be used with other types of beds.

As illustrated in FIG. 3, network bed architecture 300 is configured as a star topology with central controller 302 and firmness controller 304 functioning as the hub and articulation controller 306, temperature controller 308, external network device 310, remote controls 312, 314, and voice controller 316 functioning as possible spokes, also referred to herein as components. Thus, in various examples, central controller 302 acts a relay between the various components.

In yet another example, central controller 302 listens to communications (e.g., control signals) between components even if the communication is not being relayed through central controller 302. For example, consider a user sending a command using remote 312 to temperature controller 308. Central controller 302 may listen for the command and check to determine if instructions are stored at central controller 302 to override the command (e.g., it conflicts with a previous setting). Central controller 302 may also log the command for future use (e.g., determining a pattern of user preferences for the components).

In other examples, different topologies may be used. For example, the components and central controller 302 may be configured as a mesh network in which each component may communicate with one or all of the other components directly, bypassing central controller 302. In various examples, a combination of topologies may be used. For example, remote controller 312 may communicate directly to temperature controller 308 but also relay the communication to central controller 302.

In various examples, the controllers and devices illustrated in FIG. 3 may each include a processor, a storage device, and a network interface. The processor may be a general purpose central processing unit (CPU) or application-specific integrated circuit (ASIC). The storage device may include volatile or non-volatile static storage (e.g., Flash memory, RAM, EPROM, etc.). The storage device may store instructions which, when executed by the processor, configure the processor to perform the functionality described herein. For example, a processor of firmness control 304 may be configured to send a command to a relief valve to decrease the pressure in a bed.

In various examples, the network interface of the components may be configured to transmit and receive communications in a variety of wired and wireless protocols. For example, the network interface may be configured to use the 802.11 standards (e.g., 802.11a/b/c/g/n/ac), PAN network standards such as 802.15.4 or Bluetooth, infrared, cellular standards (e.g., 3G/4G etc.), Ethernet, USB for receiving and transmitting data, and powerline networking. The previous list is not intended to exhaustive and other protocols may be used. Not all components of FIG. 3 need to be configured to use the same protocols. For example, remote control 312 may communicate with central controller 302 via Bluetooth while temperature controller 308 and articulation controller 306 are connected to central controller using 802.15.4. Within FIG. 3, the lightning connectors represent wireless connections and the solid lines represent wired connections, however, the connections between the components is not limited to such connections and each connection may be wired or wireless.

Moreover, in various examples, the processor, storage device, and network interface of a component may be located in different locations than various elements used to affect a command. For example, as in FIG. 1, firmness controller 302 may have a pump that is housed in a separate enclosure than the processor used to control the pump. Similar separation of elements may be employed for the other controllers and devices in FIG. 3.

In various examples, firmness controller 304 is configured to regulate pressure in an air mattress. For example, firmness controller 304 may include a pump such as described with reference to FIG. 2 (see e.g., pump 20). Thus, in an example, firmness controller 304 may respond to commands to increase or decrease pressure in the air mattress. The commands may be received from another component or based on stored application instructions that are part of firmness controller 304.

As illustrated in FIG. 3 central controller 302 includes firmness controller 304 and pump 305. Thus, in an example, the processor of central controller 302 and firmness control 304 may be the same processor. Furthermore, the pump may also be part of central controller 302. Accordingly, central controller 302 may be responsible for pressure regulation as well as other functionality as described in further portions of this disclosure.

In various examples, articulation controller 306 is configured to adjust the position of a bed (e.g., bed 301) by adjusting the foundation that supports the bed. In an example, separate positions may be set for two different beds (e.g., two twin beds placed next to each other). The foundation may include more than one zone that may be independently adjusted. Articulation control 306 may also be configured to provide different levels of massage to a person on the bed.

In various examples, temperature controller 308 is configured to increase, decrease, or maintain the temperature of a user. For example, a pad may be placed on top of or be part of the air mattress. Air may be pushed through the pad and vented to cool off a user of the bed. Conversely, the pad may include a heating element that may be used to keep the user warm. In various examples, the pad includes the temperature sensor 309 and temperature controller 308 receives temperature readings from the temperature sensor 309. In other examples, the temperature sensor 309 can be separate from the pad, e.g., part of the air mattress or foundation.

In various examples, additional controllers may communicate with central controller 302. These controllers may include, but are not limited to, illumination controllers for turning on and off light elements placed on and around the bed and outlet controllers for controlling power to one or more power outlets. In some examples, one or more of these controllers can be located offsite, e.g., cloud computing implementations.

In various examples, external network device 310, remote controllers 312, 314 and voice controller 316 may be used to input commands (e.g., from a user or remote system) to control one or more components of architecture 300. The commands may be transmitted from one of the controllers 312, 314, or 316 and received in central controller 302. Central controller 302 may process the command to determine the appropriate component to route the received command. For example, each command sent via one of controllers 312, 314, or 316 may include a header or other metadata that indicates which component the command is for. Central controller 302 may then transmit the command via central controller 302's network interface to the appropriate component.

For example, a user may input a desired temperature for the user's bed into remote control 312. The desired temperature may be encapsulated in a command data structure that includes the temperature as well as identifies temperature controller 308 as the desired component to be controlled. The command data structure may then be transmitted via Bluetooth to central controller 302. In various examples, the command data structure is encrypted before being transmitted. Central controller 302 may parse the command data structure and relay the command to temperature controller 308 using a PAN. Temperature controller 308 may be then configured its elements to increase or decrease the temperature of the pad depending on the temperature originally input into remote control 312.

In various examples, data may be transmitted from a component back to one or more of the remote controls. For example, the current temperature as determined by a sensor element of temperature controller 308, e.g., temperature sensor 309, the pressure of the bed, the current position of the foundation or other information may be transmitted to central controller 302. Central controller 302 may then transmit the received information and transmit it to remote control 312 where it may be displayed to the user. In some examples, the data can be transmitted to a customer service center to help diagnose a problem with system.

In various examples, multiple types of devices may be used to input commands to control the components of architecture 300. For example, remote control 312 may be a mobile device such as a smart phone or tablet computer running an application. Other examples of remote control 312 may include a dedicated device for interacting with the components described herein. In various examples, remote controls 312/314 include a display device for displaying an interface to a user. Remote control 312/314 may also include one or more input devices. Input devices may include, but are not limited to, keypads, touchscreen, gesture, motion and voice controls.

Remote control 314 may be a single component remote configured to interact with one component of the mattress architecture. For example, remote control 314 may be configured to accept inputs to increase or decrease the air mattress pressure. Voice controller 316 may be configured to accept voice commands to control one or more components. In various examples, more than one of the remote controls 312/314 and voice controller 316 may be used.

With respect to remote control 312, the application may be configured to pair with one or more central controllers. For each central controller, data may be transmitted to the mobile device that includes a list of components linked with the central controller. For example, consider that remote control 312 is a mobile phone and that the application has been authenticated and paired with central controller 302. Remote control 312 may transmit a discovery request to central controller 302 to inquiry about other components and available services. In response, central controller 302 may transmit a list of services that includes available functions for adjusting the firmness of the bed, position of the bed, and temperature of the bed. In various embodiments, the application may then display functions for increasing/decreasing pressure of the air mattress, adjusting positions of the bed, and adjusting temperature. If components are added/removed to the architecture under control of central controller 302, an updated list may be transmitted to remote control 312 and the interface of the application may be adjusted accordingly.

In various examples, central controller 302 is configured as a distributor of software updates to components in architecture 300. For example, a firmware update for temperature controller 308 may become available. The update may be loaded into a storage device of central controller 302 (e.g., via a USB interface or using wireless techniques). Central controller 302 may then transmit the update to temperature controller 308 with instructions to update. Temperature controller 308 may attempt to install the update. A status message may be transmitted from temperature controller 308 to central controller 302 indicating the success or failure of the update.

In various examples, central controller 302 is configured to analyze data collected by a pressure transducer (e.g., transducer 46 with respect to FIG. 2) to determine various states of a person lying on the bed. For example, central controller 302 may determine the heart rate or respiration rate, motion, presence, arrhythmias, apneas, and sleep state of a person lying in the bed. Additional processing may be done using the collected data to determine a possible sleep state of the person. For example, central controller 302 may determine when a person falls asleep and, while asleep, the various sleep states of the person.

In various examples, external network device 310 includes a network interface to interact with an external server for processing and storage of data related to components in architecture 300. For example, the determined sleep data as described above may be transmitted via a network (e.g., the Internet) from central controller 302 to external network device 310 for storage. In an example, the pressure transducer data may be transmitted to the external server for additional analysis. The external network device 310 may also analyze and filter the data before transmitting it to the external server.

In an example, diagnostic data of the components may also be routed to external network device 310 for storage and diagnosis on the external server. For example, if temperature controller 308 (or a leak detector or system health monitor) detects an abnormal temperature reading (e.g., a drop in temperature over one minute that exceeds a set threshold) diagnostic data (sensor readings, current settings, etc.) may be wireless transmitted from temperature controller 308 to central controller 302. Central controller 302 may then transmit this data via USB to external network device 310. External device 310 may wirelessly transmit the information to a WLAN access point where it is routed to the external server for analysis.

Example Machine Architecture and Machine-Readable Medium

Figure 4:
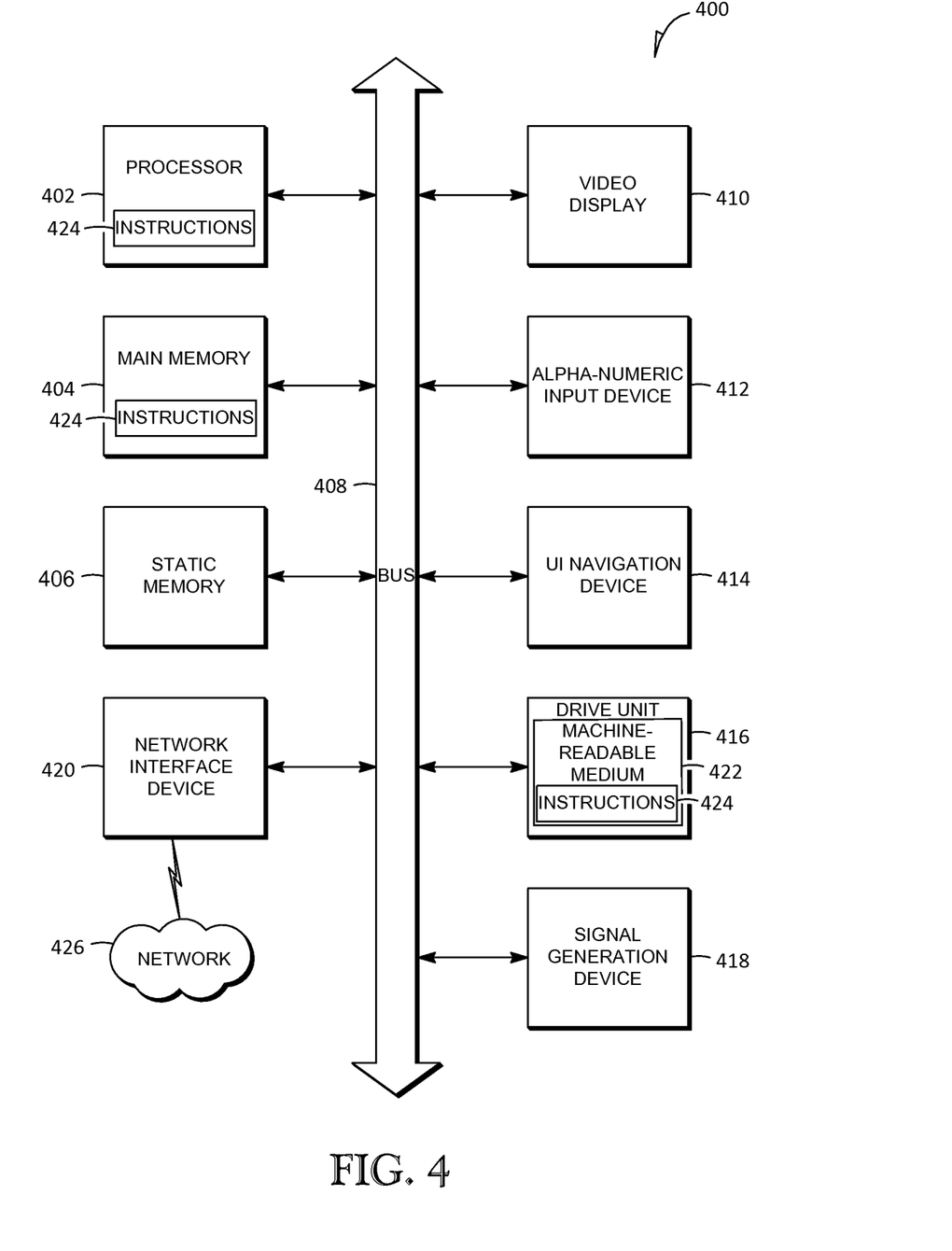
FIG. 4 is a block diagram of machine in the example form of a computer system within which a set instructions, for causing the machine to perform any one or more of the methodologies discussed herein, may be executed.

FIG. 4 is a block diagram of machine in the example form of a computer system 400 within which instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In some examples, one or more of machines can be located offsite, e.g., cloud computing implementations.

The example computer system 400 includes a processor 402 (e.g., a central processing unit (CPU), a graphics processing unit (GPU), ASIC or a combination), a main memory 404 and a static memory 406, which communicate with each other via a bus 408. The computer system 400 may further include a video display unit 410 (e.g., a liquid crystal display (LCD) or a cathode ray tube (CRT)). The computer system 400 also includes an alphanumeric input device 412 (e.g., a keyboard and/or touchscreen), a user interface (UI) navigation device 414 (e.g., a mouse), a disk drive unit 416, a signal generation device 418 (e.g., a speaker) and a network interface device 420.

Machine-Readable Medium

The disk drive unit 416 includes a machine-readable medium 422 on which is stored one or more sets of instructions and data structures (e.g., software) 424 embodying or utilized by any one or more of the methodologies or functions described herein. The instructions 424 may also reside, completely or at least partially, within the main memory 404 and/or within the processor 402 during execution thereof by the computer system 400, the main memory 404 and the processor 402 also constituting machine-readable media.

While the machine-readable medium 422 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

Transmission Medium

The instructions 424 may further be transmitted or received over a communications network 426 using a transmission medium. The instructions 424 may be transmitted using the network interface device 420 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Alarm Techniques

In addition to the techniques described above, this disclosure is directed to techniques for waking a user by changing the user's sleep environment. As described in more detail below, by changing the user's sleep environment, e.g., air mattress pressure, air mattress foundation motion, temperature, the techniques of this disclosure can provide the user with a "minimally invasive" alarm system that gently wakes the user, in contrast with an alarm clock, for example.

In one example, the user can set a desired time and method for waking via a user interface (or "alarm settings"), e.g., remote controllers 312, 314 or voice controller 316. In some examples, the user can set a desired time and method for waking via a web portal connected to the Internet. In response to receiving the user's alarm settings, the web portal can communicate the user's desired wake setting(s) to the central controller 302 via the Internet to a WiFi module, for example, in communication with the central controller 302. In some examples, upon receiving the user settings, the central controller 302 can store the settings in a memory device.

In one example implementation, the user can choose to change the pressure of one or more air chambers, e.g., air chambers 14A, 14B of FIG. 2, of the mattress as a method for waking. For example, the user may program the system architecture 300 and, in particular, the central controller 302, to increase the pressure in an air chamber via the firmness controller 304 at a particular time, e.g., in order to wake the user by way of a minimally invasive alarm.

In another example implementation, the user can choose to adjust the position of the bed and/or add motion to the bed, e.g., via a massage function, as a method for waking For example, the user may program the system architecture 300 and, in particular, the central controller 302, to transmit instructions to the articulation controller 306 at a particular time. In response, the articulation controller 306 can adjust the foundation of the bed 301, e.g., in a manner specified by the user during programming or in a default manner, to move from its current position to another, different position. Alternatively or in addition to adjusting the position of the foundation of the bed 301, the articulation controller can provide the user with one or more levels of massage, e.g., in order to wake the user by way of a minimally invasive alarm.

In another example implementation, the user can choose to adjust the temperature of the bed as a method for waking. For example, the user may program the system architecture 300 and, in particular, the central controller 302, to transmit instructions to the temperature controller 308 at a particular time. In response, the temperature controller 308 can adjust the temperature of the user, e.g., via a cooling or heating mechanism provided by a pad placed on top of or forming a part of the air mattress e.g., in order to wake the user by way of a minimally invasive alarm.

Although the minimally invasive techniques for waking a user were described above separately, each of the described techniques can be used in combination with one another, as desired. For example, a user may program the central controller 302 to provide an alarm function that includes changes to both air mattress pressure and temperature. Or, a user may program the central controller 302 to provide an alarm function that includes changes to both air mattress pressure and temperature and that further includes adjusting the position of and/or providing motion to the foundation of the bed 301.

In some example implementations, the user can program two or more minimally invasive techniques for waking the user in a pattern, e.g., one after another. For example, the user can program the central controller 302 to provide an alarm function that initially changes the pressure of one or more air chambers, e.g., air chambers 14A, 14B of FIG. 2, and then change the temperature of the user a predetermined period of time after the change to the pressure of the air chambers. In addition, the user can, for example, program the central controller 302 to control the articulation controller 306 to adjust the foundation of the bed 301 a period of time after changing the temperature or, in some examples, substantially simultaneously with changing the temperature. In this manner, a waking function pattern can be achieved by sequentially or progressively changing various aspects of the user's sleep environment.

In some examples, presence detection can be included in order to prevent an alarm from occurring or terminate an alarm in progress. For example, the pressure transducer 46 (of FIG. 2) can be used to detect the user's presence within the bed 301, e.g., via a gross pressure change determination and/or via one or more of a respiration rate signal, heart rate signal, and/or other biometric signals. Upon determining that the user has gotten out of bed, e.g., via a gross pressure change determination, the central controller 302 can terminate any active minimally invasive alarms, e.g., changes to pressure, temperature, motion of the foundation, etc. In other examples, upon determining that the user is not present in the bed, e.g., the user is away on a business trip, the central controller 302 can prevent any pending minimally invasive alarms from occurring, e.g., changes to pressure, temperature, motion of the foundation, etc.

This disclosure is not limited to the example minimally invasive alarms mentioned above. In addition to changes to pressure, temperature, and motion of the foundation, other example minimally invasive alarms include, but are not limited to, changes to lighting, e.g., turning lights on/off as well as opening and/or closing window shades, turning on/off a television, and turning on/off a sound system.

Figure 5:
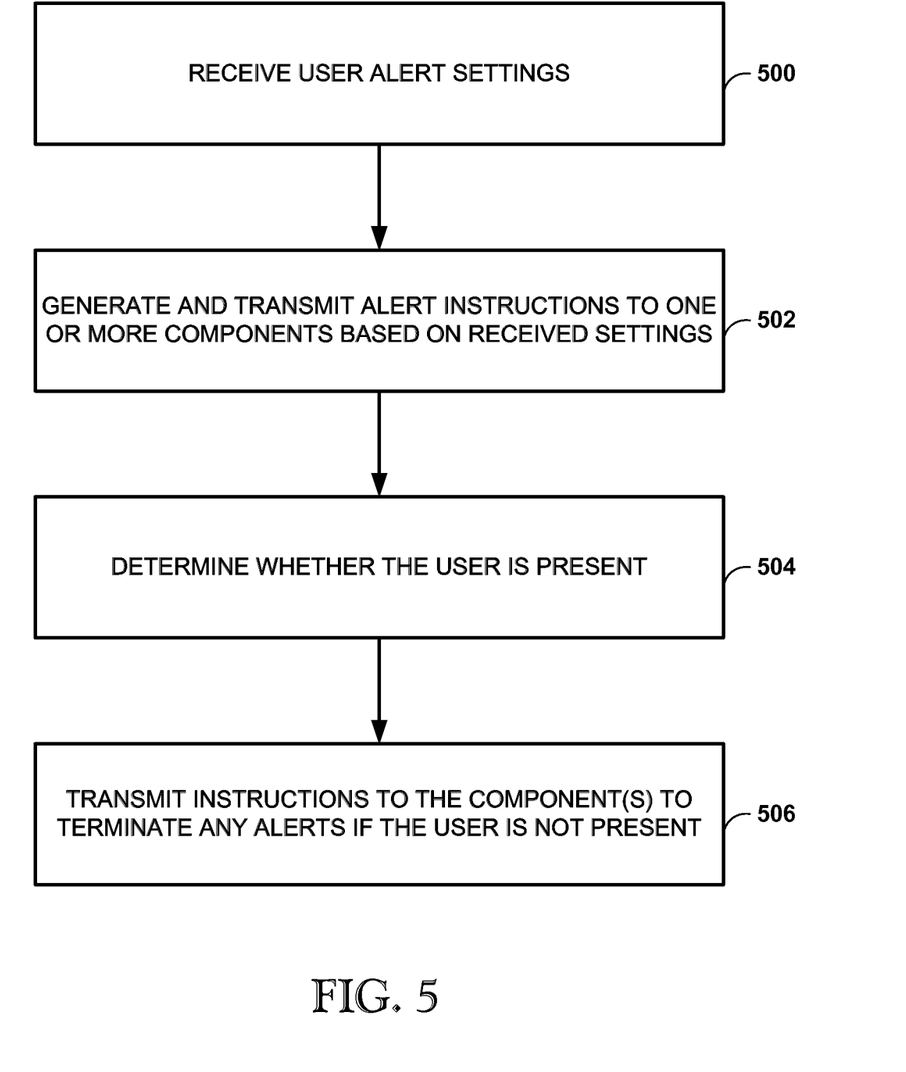
FIG. 5 is a flow diagram depicting an example method of waking a person by changing the person's sleep environment, in accordance with various techniques of this disclosure.

FIG. 5 is a flow diagram depicting an example method of waking a person by changing the person's sleep environment. In FIG. 5, the central controller 302 receives alarm settings from a user, e.g., via a user interface such as the remote controllers 312, 314, voice controller 316, or via a web portal connected to the Internet (500). In response to receiving the user's alarm settings, e.g., a time and method for waking, the central controller 302 transmits alarm instructions to one or more components of the bed system, e.g., firmness controller 304, articulation controller 306, and temperature controller 308, based on the received user alarm settings (502). Upon receiving the instructions, the component(s) operate to change the user's sleep environment, e.g., change the air pressure in a chamber, change the temperature, etc.

In some examples the method of FIG. 5 further includes determining whether the user is present in the bed (504). For example, the central controller 302 can determine whether a user is present using a change in gross pressure as using received pressure signals from the pressure transducer 46 of FIG. 2. If the central controller 302 determines that the user is not present, the central controller 302 can transmit instructions to the component(s) of the bed system to terminate any active alarms.

In some examples, presence can be determined using the presence of human or animal biosignals.

In one example implementation, the central controller 302 can detect user presence using temperature changes detected in the mattress, e.g., using one or more temperature sensors positioned in or on the mattress. The temperature sensors and the central controller 302 can detect a rise in temperature, e.g., over a specified period of time, and determine that a user is present in the bed. For example, if the central controller 302 detects a rise in temperature and then determines that the detected rise in temperature was not caused by the system's temperature controller 308, the central controller 302 can determine that the user is present.

In addition to the techniques described above, this disclosure is directed to techniques for waking a user using a biometric alarm system. As indicated above, the central controller 302 can determine a user's sleep state, e.g., rapid eye movement ("REM") or non-rapid eye movement ("NREM"). The central controller 302 can determine a user's sleep state by using various biometric signals such as heart rate, respiration, and/or movement of the user. Techniques for monitoring a user's sleep using heart rate information, respiration rate information, and other user information are disclosed in U.S. patent application Publication No. 20100170043 to Steven J. Young et al., titled "APPARATUS FOR MONITORING VITAL SIGNS," the entire content of which is incorporated herein by reference. Using various techniques of this disclosure, the user can set a window of time in which to wake up (or "alarm window") and allow the central controller 302 to determine the optimum time within that window to wake the user based on the determined sleep state.

By way of specific example, a user can set a desired window of time for waking of between 5:00 AM and 6:00 AM via a user interface, e.g., remote controllers 312, 314, voice controller 316, or via a web portal connected to the Internet. In some examples, upon receiving the user settings, the central controller 302 can store the settings in a memory device. While the user is sleeping, the central controller 302 can receive one or more of the user's biometric signals, e.g., heart rate, respiration, and motion, and determine the user's present sleep state based on the received biometric signals. It may be desirable to wake a person during a particular portion of a sleep cycle, e.g., in NREM sleep in contrast to REM sleep.

If the central controller 302 has determined that at the beginning of the user-defined window, e.g., 5:00 AM, the user is not in an optimum state in their sleep cycle for waking, e.g., in REM sleep, the central controller 302 can delay transmitting any instructions to one or more components of the bed system, e.g., firmness controller 304, articulation controller 306, and temperature controller 308, to activate and wake the user. Then, the central controller 302 can continue to receive one or more of the user's biometric signals and continue to determine the user's sleep state. Once the user's sleep state transitions from one portion of a sleep cycle to a more desirable portion at which to be awakened, e.g., from REM sleep to NREM sleep, the central controller 302 can transmit any instructions to one or more components of the bed system, e.g., firmness controller 304, articulation controller 306, and temperature controller 308, to activate and wake the user. In this manner, the user is awakened.

Of course, if the central controller 302 has determined that at the beginning of the user-defined window, e.g., 5:00 AM, the user is in an optimum state for waking based on the determine sleep cycle, e.g., NREM sleep, the central controller 302 can transmit any instructions to one or more components of the bed system, e.g., firmness controller 304, articulation controller 306, and temperature controller 308, to activate and wake the user. In this manner, the user is awakened.

In some examples, if the central controller 302 has determined that the user is still in REM sleep once the end of the user-defined window has been reached (thus not in an optimum sleep state for waking), then the central controller 302 will nevertheless wake the user. That is, once the end of the user-defined window has been reached, e.g., 6:00 AM in the example above, the central controller 302 can transmit any instructions to one or more components of the bed system, e.g., firmness controller 304, articulation controller 306, and temperature controller 308, to activate and wake the user even if the user is not in an optimum sleep state.

Figure 6:
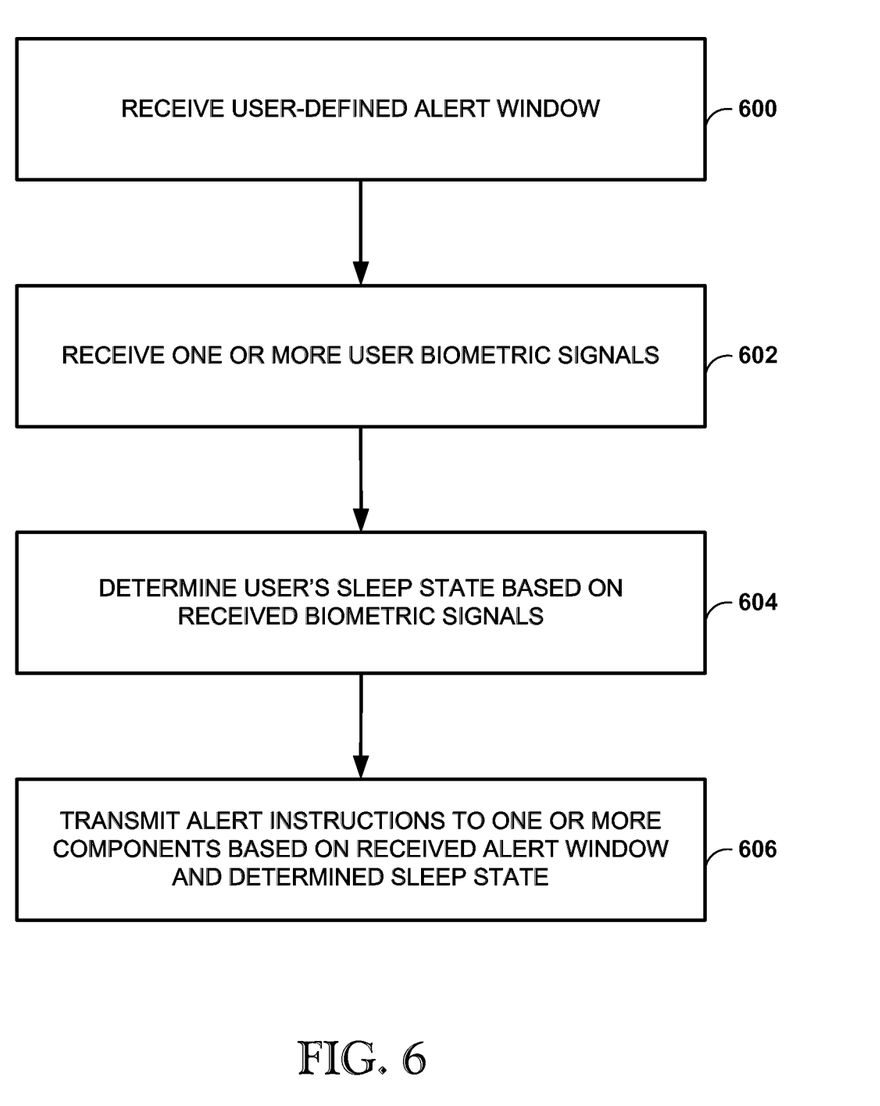
FIG. 6 is a flow diagram depicting an example method of waking a person using biometric signals, in accordance with various techniques of this disclosure.

FIG. 6 is a flow diagram depicting an example method of waking a person using biometric signals. In FIG. 6, the central controller 302 receives a user-defined alarm window from a user, e.g., via a user interface such as the remote controllers 312, 314, voice controller 316, or via web portal connected to the Internet (600), indicating a desired window of time in which to wake up, e.g., 5:00 AM to 6:00 AM. The central controller 302 can receive biometric signals of the user, such as heart rate, respiration, and/or motion signals, via the pressure transducer 46 of FIG. 2 (602).

Using the received biometric signal(s), the central controller 302 can determine the user's present sleep state, e.g., REM or NREM (604). If the central controller 302 determines that the user is in an optimum sleep state, e.g., NREM, and that the current time is within the user-defined alarm window, then the central controller 302 can transmit alarm instructions to one or more components of the bed system, e.g., firmness controller 304, articulation controller 306, and temperature controller 308 to wake the user (606).

In some example implementations, if the central controller 302 determines that the user is not an optimum sleep state, e.g., REM, and that the current time is beyond the user-defined alarm window, then the central controller 302 can nevertheless transmit alarm instructions to one or more components of the bed system, e.g., firmness controller 304, articulation controller 306, and temperature controller 308 to wake the user within the defined window of time.

In some examples, the biometric signal(s) can be processed by another device or component instead of by the central controller 302, e.g., remote server. In such an implementation, the other device or component can process the biometric signal(s) and transmit a signal representing the processed signal to the central controller 302. Then, the central controller 302 can determine a sleep state based on the received signal. Or, in other examples, the other device or component can process the biometric signal(s), determine the sleep state of the user, and transmit a signal representing the determined sleep state to the central controller 302.

Remote Monitoring Techniques

In addition to the techniques described above, this disclosure is directed to remote monitoring techniques. Using various techniques of this disclosure, a first bed system 300 can detect when a first user of the first bed system 300, e.g., a child in a first room, is out of bed and, in response to detecting that the first user is out of bed, transmit an alert signal to a second bed system 300 that can alert a second user of the second bed system, e.g., a parent in a second room, that the first user is out of bed.

In one example implementation, the bed system can detect whether a user is out of the bed using a presence detection technique. For example, the pressure transducer 46 (of FIG. 2) can be used to detect the user's presence within the bed 301, e.g., via a gross pressure change determination, presence of biosignals, or a vision system. Upon determining that the user has gotten out of bed, e.g., via a gross pressure change determination, the central controller 302 of the first bed system can generate and transmit one or more instructions that, when received and executed by a central controller 302 of a second bed system, can cause one or more components of the second bed system to alert a user of the second bed system, e.g., changes to pressure, temperature, motion of the foundation, etc. The instruction(s) from the first central controller 302 to the second central controller 302 using wired or wireless techniques and protocols, some of which are described above.

By way of specific example, upon determining that a first user, e.g., child, has gotten out of bed, the central controller 302 of the first bed system can generate and transmit an instruction that, when received and executed by a central controller 302 of a second bed system, can cause the articulation controller 306 of the second bed system to move the foundation of the second bed system in order to alert the user of the second bed system, e.g., parent, that the first user is out of bed. In other examples, the instruction generated and transmitted by the central controller 302 of the first bed system can alternatively or additionally cause the temperature controller 308 of the second bed system and/or the firmness controller 304 of the second bed system to change temperature or pressure, respectively, of the second bed system.

The disclosure is not limited to these specific components for alerting a user of the second bed system. Instead, the central controller 302 can, for example, be used to turn lights on/off, open and/or close window shades, turn on/off a television, and turn on/off a sound system.

Figure 7:
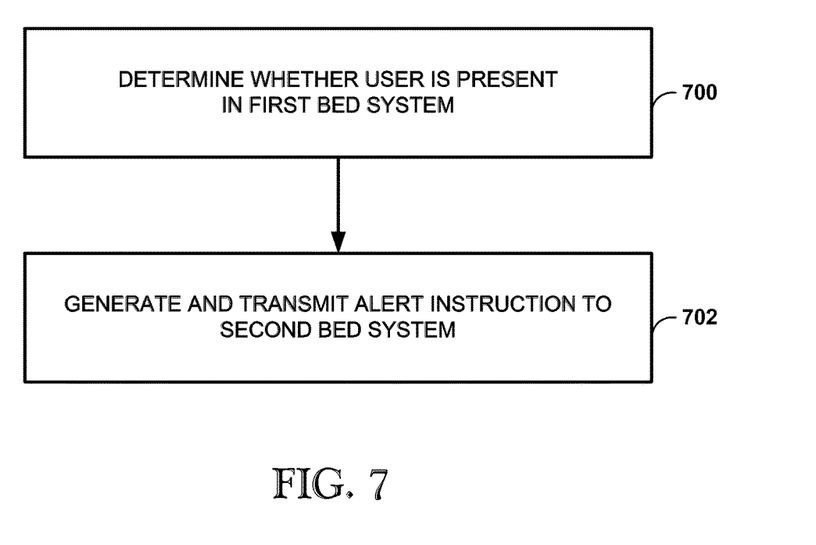
FIG. 7 is a flow diagram depicting an example method of remote monitoring, in accordance with various techniques of this disclosure.

FIG. 7 is a flow diagram depicting an example method of remote monitoring, in accordance with various techniques of this disclosure. In FIG. 7, a central controller 302 of a first bed system can determine whether a user of the first bed system, e.g., a child, is present (700). For example, the central controller 302 of the first bed system can use a gross pressure change technique to determine presence. If the central controller 302 of the first bed system determines that the user has gotten out of the bed, the central controller 302 generates and transmits an instruction that, when received and executed by a central controller 302 of a second bed system, can one or more instructions that, when received and executed by a central controller 302 of a second bed system, can cause one or more components of the second bed system to alert a user of the second bed system, e.g., changes to pressure, temperature, motion of the foundation, etc.

Although an embodiment has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled. As it common, the terms "a" and "an" may refer to one or more unless otherwise indicated.

The invention claimed is:

1. A method comprising:
   determining, at a first central controller of a first air mattress system, that a mattress of the first air mattress system does not have a user present, wherein the first central controller of the first air mattress system is configured to communicate with elements of the first air mattress system to facilitate function of the first air mattress system, wherein a second air mattress system comprises a second central controller of the second air mattress system, wherein the second central controller of the second air mattress system is configured to communicate with elements of the second air mattress system to facilitate function of the second air mattress system, wherein the first central controller of the first air mattress system is configured to communicate via one or more communication networks to transmit and receive instructions, wherein the second central controller of the second air mattress system is configured to communicate via one or more communication networks to transmit and receive instructions;
   responsive to determining that the mattress of the first air mattress system does not have a user present, generating, at the first central controller of the first air mattress system, an instruction to adjust a feature of a component of a second air mattress system that is remote from the first air mattress system;
   transmitting, on a communication network by the first central controller of a first air mattress system, the instruction to adjust the feature of the component of the second air mattress system such that the instruction is routed to the second central controller of the second air mattress system; and
   adjusting, by the second central controller, responsive to receiving the instruction, the feature of the component of the second air mattress system such that the user of the second air mattress system is awakened by the adjustment of the feature of the component of the second air mattress system in response to the first central controller determining that the first air mattress does not have a user present.

2. The method of claim 1, wherein determining, at the first central controller of the first air mattress system, that a mattress of the first air mattress system does not have a user present comprises:

detecting a gross pressure change of the first air mattress system.

3. The method of claim 1, wherein determining, at the first central controller of the first air mattress system, that a mattress of the first air mattress system does not have a user present comprises:
detecting a lack of a biometric signal.

4. The method of claim 1, wherein determining, at the first central controller of the first air mattress system, that a mattress of the first air mattress system does not have a user present comprises:
detecting a temperature change.

5. The method of claim 1, wherein the instruction to adjust the feature of the component of the second air mattress system is configured to alert a user of the second air mattress system.

6. The method of claim 1, wherein the instruction to adjust the feature of the component of the second air mattress system is an instruction to change gross pressure of an air mattress of the second air mattress system.

7. The method of claim 1, wherein the instruction to adjust the feature of the component of the second air mattress system is an instruction to change temperature of the component of the second air mattress system.

8. The method of claim 1, wherein the instruction to adjust the feature of the component of the second air mattress system is an instruction to adjust a foundation of the second air mattress systems.

9. A sleep system comprising:
a first air mattress system comprising:
an first air mattress; and
a first central controller configured to:
communicate with elements of the first air mattress system to facilitate function of the first air mattress system;
communicate via one or more communication networks to transmit and receive instructions;
determine that the first air mattress does not have a user present;
responsive to determining that the first air mattress of the first air mattress system does not have a user present, generate an instruction to adjust a feature of a component of a second air mattress system that is remote from the first air mattress system; and
transmit on a communication network by the first central controller of a first air mattress system, the instruction to adjust the feature of the component of the second air mattress system such that the instruction is routed to a second central controller of the second air mattress system; and
the second air mattress system comprising:
the second central controller configured to:
communicate with elements of the second air mattress system to facilitate function of the second air mattress system; and
communicate via one or more communication networks to transmit and receive instructions.

10. The sleep system of claim 9, wherein the second central controller is further configured to:
receive the instruction to adjust the feature of the component of the second air mattress system; and
responsive to receiving the instruction to adjust the feature of the component of the second air mattress system, adjust the component of the second air mattress system.

11. The sleep system of claim 9, wherein, to determine that the first air mattress does not have a user present, the first central controller is configured to detect a gross pressure change.

12. The sleep system of claim 9, wherein, to determine that the first air mattress does not have a user present, the first central controller is configured to detect a lack of a biometric signal.

13. The sleep system of claim 9, wherein, to determine that the first air mattress does not have a user present, the first central controller is configured to detect a temperature change.

14. The sleep system of claim 9, wherein the instruction to adjust the feature of the component of the second air mattress system is configured to alert a user of the second air mattress system.

15. The sleep system of claim 9, wherein the instruction to adjust the feature of the component of the second air mattress system is an instruction to change gross pressure of an air mattress of the second air mattress system.

16. The sleep system of claim 9, wherein the instruction to adjust the feature of the component of the second air mattress system is an instruction to change temperature of the component of the second air mattress system.

17. The sleep system of claim 9, wherein the instruction to adjust the feature of the component of the second air mattress system is an instruction to adjust a foundation of the second air mattress systems.

18. A sleep system comprising:
a first air mattress system comprising:
an first air mattress; and
a first central controller configured to:
determine that the first air mattress does not have a user present;
responsive to determining that the first air mattress of the first air mattress system does not have a user present, generate an instruction to adjust a feature of a component of a second air mattress system that is remote from the first air mattress system; and
transmit the instruction to adjust the feature of the component of the second air mattress system;
the second air mattress system comprising:
a second central controller configured to:
receive the instruction to adjust the feature of the component of the second air mattress system; and
responsive to receiving the instruction to adjust the feature of the component of the second air mattress system, adjust the component of the second air mattress system;
determine that the second air mattress system does not have a second user present; and
prevent adjustment of the feature of the component of the second air mattress system in response to determining that the second air mattress system does not have the second user present.

19. The method of claim 1, the method further comprising:
determining that the second air mattress system does not have a second user present; and
preventing adjustment of the feature of the component of the second air mattress system in response to determining that the second air mattress system does not have the second user present.

20. The method of claim 1, wherein the first air mattress system is in a first room, wherein the second air mattress system is a mattress system for a caregiver in a second room, and wherein the second air mattress system is connected via a wireless network connection to the first air mattress to alert the caregiver when the user is out of bed.

21. The method of claim 1, wherein the method further comprises determining that the mattress of the first air mattress system does not have a user present.

22. The method of claim 21, wherein determining that the mattress of the first air mattress system does not have a user present comprises sensing air pressure of the mattress with a pressure transducer; and
wherein generating, at the first central controller of the first air mattress system, an instruction to adjust a feature of a component of a second air mattress system that is remote from the first air mattress system is performed responsive to sensing air pressure of the mattress with a pressure transducer.

23. The sleep system of claim 9, wherein the first central controller is further configured to determine that the first air mattress of the first air mattress system does not have a user present.

24. The sleep system of claim 23, wherein to determine that the first air mattress of the first air mattress system does not have a user present, the first central controller is further configured to sense air pressure of the mattress with a pressure transducer; and
wherein the first central controller is configured to generate an instruction to adjust a feature of a component of a second air mattress system that is remote from the first air mattress system in response to sensing air pressure of the mattress with a pressure transducer.

25. The sleep system of claim 9, wherein the second central controller is configured to, responsive to receiving the instruction, adjust the feature of the component of the second air mattress system such that the user of the second air mattress system is awakened by the adjustment the feature of the component of the second air mattress system in response to receiving the instruction at the second central controller.

26. The sleep system of claim 9, wherein the second central controller is configured to, responsive to receiving the instruction, adjust the feature of the component of the second air mattress system such that the user of the second air mattress system is awakened by the adjustment of the feature of the component of the second air mattress system in response to the first central controller determining that the first air mattress does not have a user present.

* * * * *